United States Patent [19] [11] 3,937,747
Thornton et al. [45] Feb. 10, 1976

[54] BALANCING ADIABATIC REACTORS

[75] Inventors: Bruce C. Thornton, Houston, Tex.;
Michael B. Albert, Bala Cynwyd; G.
Richard Worrell, Media, both of Pa.

[73] Assignee: Atlantic Richfield Company, Los Angeles, Calif.

[22] Filed: Apr. 18, 1974

[21] Appl. No.: 462,014

[52] U.S. Cl. ........ 260/680 R; 235/151.12; 252/416; 260/683.3
[51] Int. Cl.$^2$ .......................................... C07C 5/36
[58] Field of Search...... 260/680 R, 683.3; 252/416; 235/151.12

[56] References Cited
UNITED STATES PATENTS

| | | | |
|---|---|---|---|
| 3,647,909 | 3/1972 | Michaels | 260/683.3 |
| 3,760,168 | 9/1973 | Boyd | 260/669 R |

Primary Examiner—Paul M. Coughlan, Jr.
Attorney, Agent, or Firm—John R. Ewbank

[57] ABSTRACT

Butadiene is prepared by directing a $C_4$ hydrocarbon stream through seven parallel adiabatic beds. The dehydrogenation period and the regeneration period are each about 9 1/5 minutes with evacuation and purge taking about 2 3/5 minutes of the 21 minute cycle. The temperature of the regeneration gas is individually adjusted in response to the summation of deviation of targeted conversion from average conversion and reactor deviation from average conversion amongst all reactors. Moreover, such adjustment minimizes deviations of each reactor from average conversion during the previous 21 minute cycle.

The dehydrogenation effluent is mixed and sent through a common quenching zone. The quenched product stream's density varies in response to the extent of conversion, permitting measurement of conversion for each three minutes. Average conversion for each cycle is measured by averaging the conversions for such seven time periods. The density data are directed to a digital computer. the data for each 3 minute period are a composite from four reactors. Deviation from average conversion of each reactor is designated by the computer using the relationships amongst the reactor deviations and the deviations of the 3 minute periods shown in 7 simultaneous equations. The computer controls the increments of the amount of gas supplied to the regeneration gas, thus controlling the temperature of the regeneration gas in response to the summation of such reactor's deviation from average conversion during the 21 minutes prior to the end of its dehydrogenation step, and the deviation of average conversion from targeted conversion for such reactor.

5 Claims, 1 Drawing Figure

BALANCING ADIABATIC REACTORS

FIELD OF THE INVENTION

This invention relates to a process for dehydrogenating hydrocarbons in a bank of adiabatic beds and to computer control systems for reliably controlling conversion without significantly risking excessive conversion in any reactor bed.

PRIOR ART

Michaels, U.S. Pat. No. 3,647,909, describes a method in which methane is burned in the regeneration gas to supplement the heat attributable to the burning of the carbonaceous deposit formed in the adiabatic bed.

In the research laboratory, the speed of response of temperature measuring instruments in a single adiabatic bed permits the operator to maintain the adiabatic bed at high conversion during a great number of cycles. It was learned at an early date that an adiabatic bed could become successively cooler or successively hotter if care were not exercised to assure that the heat absorbed by the bed during regeneration was equal to the endothermic heat of dehydrogenation. The adiabatic bed was unattractive from the economic standpoint if operated at too low a temperature providing a disadvantageously low conversion. The catalyst in the adiabatic bed had a very short life if operated at an excessively high temperature sometimes called sintering temperature, at which momentarily high conversion was attainable. As the catalyst was used, the temperature necessary for commercially acceptable conversion increased, so that just before a turnaround for catalyst replacement, the reactors have been operated at temperatures significantly higher than could be recommended for fresh catalyst. Thus, an operator needed to keep each bed within an appropriate temperature range, but the range shifted upwardly as the time for catalyst replacement approached.

Although the laboratory tests with adiabatic beds permit the operators to achieve high conversions, difficulties were encountered in commercial plants because operators tended to maintain bed temperatures which were adequately safe, thus avoiding rapid damage to the catalyst but producing less butadiene than theoretically possible at the very narrow temperature range of stable maximum conversion for the current catalyst. It has been customary to set the same targeted conversion for each reactor in a bank of reactors and to seek balanced performance amongst all reactors. As the catalyst aged, differences amongst reactors were detectable but there was no adequate method for measuring instantaneous fluctuations in the imbalance amongst the reactors. The type of temperature measuring devices employed industrially in the adiabatic beds tended to be slow in responding to small variations in operating conditions. Plants for making butadiene from a $C_4$ hydrocarbon stream by the adiabatic process have directed the feedstock to a bank of reactors, and the hydrocarbon effluent from each reactor has been sent through a single quench system to provide a product stream from the bank of reactors. Similarly, the air heater for a bank of reactors has supplied hot regeneration gas to a plurality of reactors simultaneously, with the cycle timer opening and closing the valves between the reactors and the manifolds from the air heater.

When butane is converted to butadiene two moles of hydrogen are formed per mole of butadiene, forming three moles in the product stream, thus providing an average molecular weight which is approximately that of the butane feedstock. Various approaches have been used for measuring the extent of conversion in the merged product stream from a bank of reactor beds. Such measurement may be a measurement of the hydrogen content, a measurement of the molecular weight, or other suitable indication of the extent of conversion. Particular advantages accrue from the use of instruments for measuring the gas density.

Many butadiene plants have been monitored by recording the reactor temperature fluctuations of the several reactors. It is also possible to monitor a butadiene plant by using charts recording fluctuations in gas density in the mixed, quenched product stream derived from a bank of n reactors, n being the number (e.g., 3 to 8) of reactors. In the development of the present invention, it was observed that there are n instances of minimum density per cycle time. Shortly after a perfect start-up subsequent to installing fresh catalyst, an adequately satisfactory balance amongst the n reactors can be achieved and evidenced by the charting of uniform minima of density of the quenched, mixed effluent.

After the brief use of fresh catalyst and until just prior to replacing the catalyst, it becomes increasingly difficult to approach perfect balance amongst the reactors. The adiabatic beds are likely to have differing catalyst activities, and/or other variations amongst the reactors, leading to imbalance amongst the reactors. Although the existence of imbalance amongst the reactors has been known, earlier literature has not described any reliable procedure for identifying which reactor required what adjustment in order to restore acceptable balance amongst the reactors.

Attempts to measure the extent of conversion in the dehydrogenation effluent from each reactor prior to the quenching proved unsatisfactory. Attempts to rely upon the measurements of temperature within the reactor bed failed to prevent imbalance amongst reactors. Efforts have generally been focused upon trying to restore the bank of reactors as closely as feasible to the ideal operation contemplated after a perfect start-up with fresh catalyst. Perfect balance amongst the reactors has been a goal toward which plant operators have generally aspired. Over a period of decades, a variety of plants utilizing banks of such adiabatic beds have been operated at less than peak efficiency because of the inadequacy of methods for adjusting the post-regeneration temperature of each reactor appropriately to properly regulate the next dehydrogenation step in such reactor.

SUMMARY OF THE INVENTION

In accordance with the present invention, the amount of heat supplied to each reactor during regeneration is adjusted to promote a conversion in the subsequent cycle at a level as close as feasible to the conversion level for which such reactor is currently targeted. Such adjustment of the heat content of the regeneration is automatically responsive to a computer-generated signal. The computer employs a signal which is the summation of the deviation of the reactor from average conversion and the deviation of the average from the targeted conversion for such reactor.

In preferred embodiments of the invention, the product from each of n reactors in a bank of reactors is quenched to provide a mixed product stream, and the signals from the measurement of the density of the mixed, quenched product stream or signals from any other suitable instrument for measuring the momentary indication of extent of conversion in such mixed, quenched product stream are fed to a computer. At or near the end of the on-stream period for each reactor, the conversion data for each of the n periods of 1/nth the cycle time are employed to obtain a measured value for the average conversion during such cycle time. Data are employed concerning the conversion for each of said n periods and the deviation from average for each of said n fractional periods. Such fractional deviation data cannot be readily interpreted because it represents mixed data from several reactors. For example, if there are seven reactors, each period includes data from at least three reactors. If there is a 21 minute cycle time and a 9 1/5 minute on-stream period, then each 3 minute period includes data from three reactors, with an additional reactor (total of 4) included for a small part of the 3 minute period, but the calculations are simplified by treating the 3 minute data as if it were generated by three reactors. The relationship between the more directly measurable seven fractional deviations and the more difficulty ascertainable approximate deviations of the seven reactors can be expressed by seven simultaneous equations.

The determination of what regeneration gas temperature should be employed for a particular reactor should be made while such reactor is imminently scheduled for regeneration; that is, after the on-stream period for such reactor is more than about ⅔ complete (substantially completely offstream) but before the regeneration is more than about one-fifth complete. It is sometimes convenient to designate such reactor as the most recently offstream reactor, but such narrower terminology is intended to embrace the reactor during such period when it is imminently scheduled for regeneration. The reactor is purged after being onstream and before regeneration, but the purging period is briefer than the period during which a reactor is imminently scheduled for regeneration.

In such 21 minute cycle system, the difference between the conversion for a reactor and the average conversion during the most recent 21 minutes provides a small number which may be positive, negative, or zero, and which can be designated as an approximation of the deviation for such reactor. The computer determines the approximate deviation for the reactor from the average conversion for the previous cycle. The computer also determines the deviation of such average conversion from the targeted conversion for that reactor. Heretofore butadiene plants have ordinarily been operated with targeted conversion being adjusted for a bank of reactors, so that previously the targeted conversion for each reactor in a bank was ordinarily the same. The computer control of the present invention has the very important advantage of making feasible the setting of each reactor for its own targeted conversion. Inasmuch as the computer dows not retain a memory of what is actually the conversion achieved in a particular reactor, but relies upon a plurality of deviations from the average conversion in the bank of reactors, the deviation of a reactor's conversion from its targeted conversion is advantageously determined by the summation of the reactor's deviation from average conversion and the deviation of the reactor's targeted conversion from such average conversion. Because measurements are conducted in a stream containing product from several reactors, a relatively complicated explanation is necessary in showing that the control system urges the process in each reactor to move toward the conversion level for which each reactor is targeted.

The computer generates a signal which is a correction signal related to the summation of the corrective signal indicative of the reactor's deviation from average conversion and the corrective signal indicative of the deviation of the targeted conversion of such reactor from said average conversion. The signal reflecting the thus measured summation of said two deviations is employed by the computer to generate the signals controlling the regeneration temperature. The air heater provides a stream containing steam, carbon dioxide, and air having a temperature usually above the methane auto ignition temperature. Hence, the methane injected near a reactor may be at least partially burned before the gas stream reaches the catalyst bed. The computer signals control the steps of increments of amounts of methane and/or other modifiers introduced into the air heater and into the supplemental fuel injection jets at each reactor, thus controlling the temperature of the regeneration gas, and thus controlling the end-of-regeneration temperature of that particular reactor. Such computer control of the temperature of a particular reactor promotes a conversion in such reactor in the subsequent cycle at a level as close as feasible to the targeted conversion level.

Because there is a reasonable correlation between the data relating to the average conversions during a series of 3 minute fractions and the maximum conversions during such series, it is convenient to employ signals from a meter measuring minimum gas density (i.e., maximum conversion) during such nth fraction of cycle time, but any appropriate measurement during such nth fraction of the cycle time which reasonably is translatable as a measurement of conversion might be substituted for such minimum density measurement.

The post-regeneration temperature of each bed is the resultant of the heat from burning the coke laid down in the previous cycle and the heat from burning the controlled amount of fuel gas (generally methane) injected into the regeneration gas, and other heat transfer characteristics of the regeneration gas. Reactors are conventionally provided with structural components assuring adequate gas mixing prior to contacting the catalyst bed and assuring uniform flow of the mixed gas stream through the catalyst bed, regardless of differences in the schematic indication of gas entry zones. It is sometimes appropriate to provide a cooling gas at a moderately low temperature such as 300°F., and to inject such cooling gas to adjust the regeneration gas to the reactor at a temperature lower than the temperature of the hot gas from the air heater for the bank of reactors. Steam or compressed air are suitable examples of cooling gases. An air heater might be simultaneously sending hot air to three reactors, one with no supplemental temperature modification, one hotter than derived from the air heater becasue of injection of supplemental methane which instantly burns to heat the regeneration gas, and one cooler than the air heater because of injection of 300°F. steam which instantly mixes to cool the regeneration gas before it reaches the catalyst bed. Computer-actuated operation of the valve system for a cooling gas (e.g., steam) so nearly resembles the corresponding operation of the valve system for the supplemental fuel supplied to the mixing zone associated with each reactor that such cooling system is omitted from the drawing in an effort to make the drawing more readily understood.

In accordance with the present invention, the signal from the computer makes fine tuning adjustments of the position of the valves supplying methane and/or cooling gas to the regeneration gas for each reactor.

Any process control system can exhibit a propensity toward excessively rapid correction of detected abnormalities. By limiting the maximum adjustments for a single regeneration, greater stability of operation is achieved while still being prompt enough to avoid runaway trends of conversion. Instead of making the adjustment which should theoretically restore the reactor for producing such targeted conversion for such reactor, such theoretical adjustment is appropriately adjusted in accordance with good engineering practice for automated instrument control. The computer retains a memory of all adjustments during recent cycles.

The adjustments of the type controlled by the present invention can be relatively infrequent during desired periods of perfect balance amongst the reactors. Partly because the conversion deviations are determined for each reactor imminently scheduled for regeneration (conveniently designated as constant surveillance) any significant deviation of conversion is detected promptly. The smallness of the adjustment required for thus promptly restoring the reactor toward its targeted conversion is among the significant advantages of the invention.

The heat input of the regeneration gas can be modified less satisfactorily by gas pressure, gas volume, gas density and/or other variables different from the preferred control of the degree of opening of the methane flow regulating valves at the air heater and for each reactor. Similarly, cooling excessively hot gas to provide to a reactor regeneration gas of suitable temperature is preferably controlled by a similar system of valves for cooling steam. It is convenient to describe all such variations of the heat content of the regeneration gas for the individual reactors primarily in terms of the preferred variations in the amount of a modifying gas.

At the air heater, in which the methane flow may be responsive to an adjustable temperature regulating control, it may be convenient to direct the signal from the computer to adjust the temperature regulating control which in turn adjusts the methane valve for the air heater. If a bank of reactors were equipped with a bank of as many air heaters as reactors, then an intermittently operated air heater would be macro-adjusted and microtuned to provide the reactor with regeneration gas having the appropriately adjusted temperature.

The regulation of the control valves for the modifying gas is more readily understood than any of the other appropriate engineering approaches for attaining the desired adjustment of the temperature of the regeneration gas. Of importance is the prompt detection of an approximate reactor deviation while the reactor is imminently scheduled for regeneration and the correction of the heat input for the next regeneration to readjust toward target conversion immediately.

The flow of concepts and signals processed by the computer in several embodiments can be shown in the following chart:

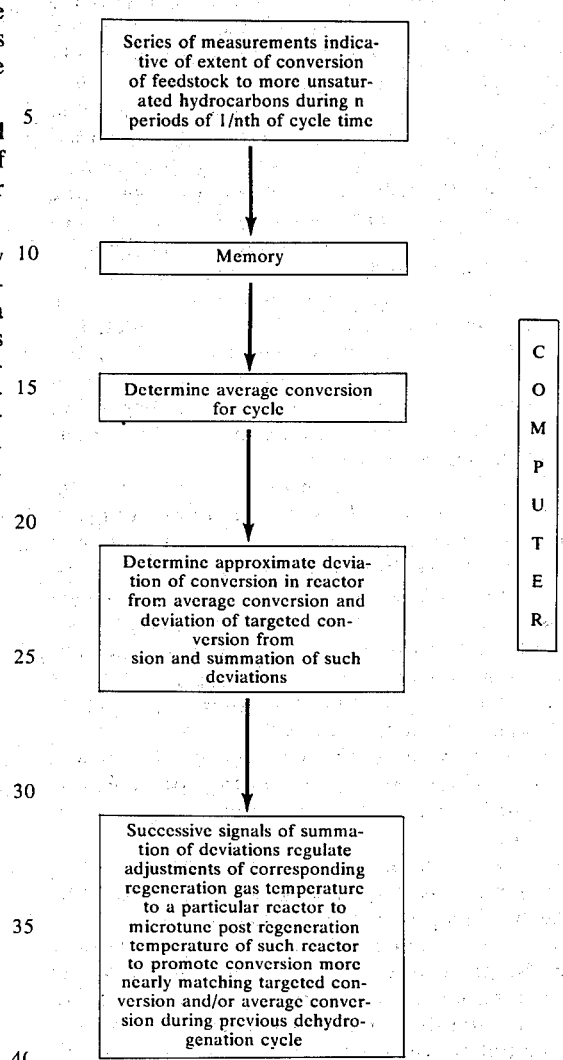

DETAILED DESCRIPTION OF DRAWINGS

Figure 1:
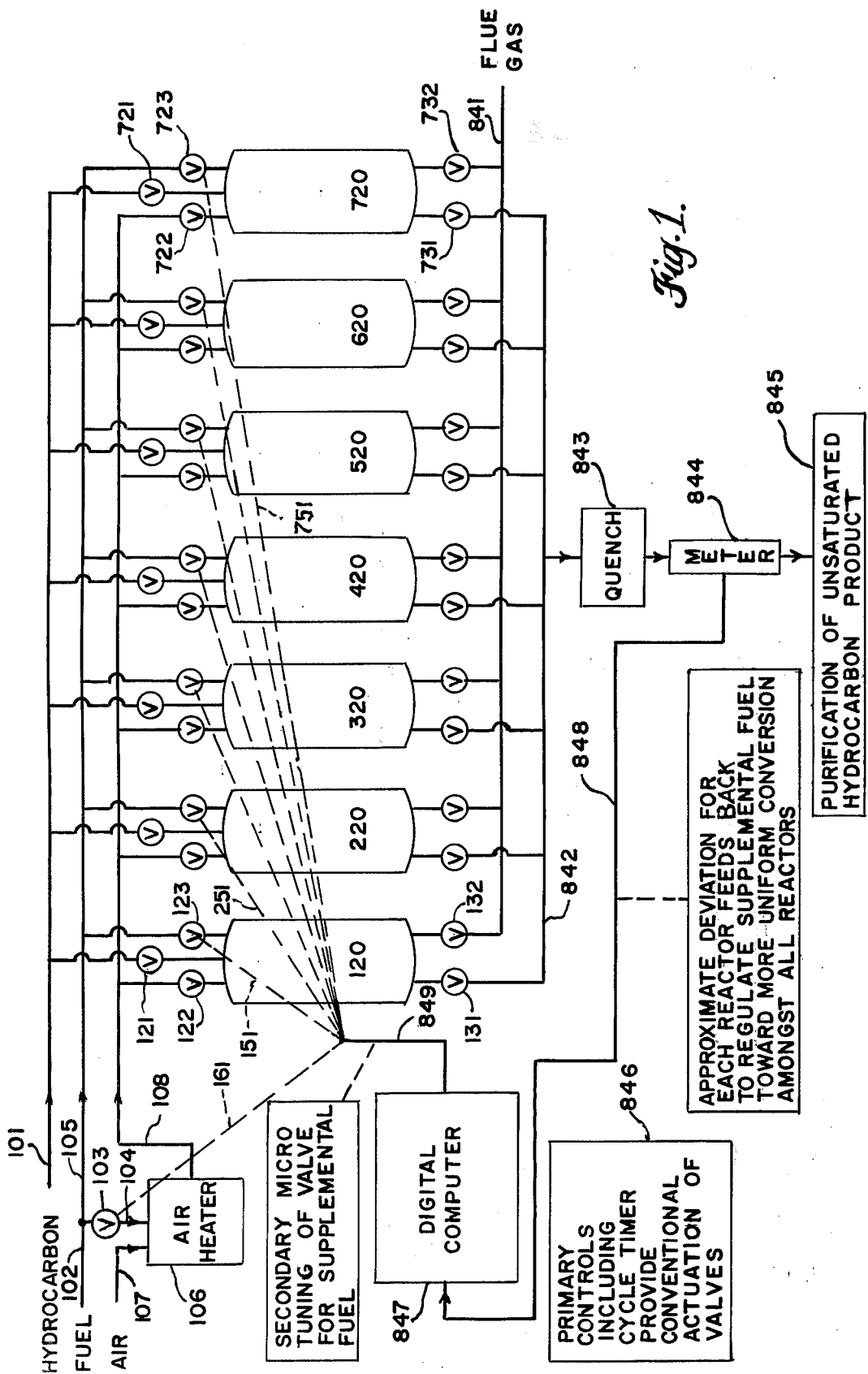
FIG. 1 is a schematic flow sheet indicating the manner in which a signal from a meter measuring the conversion of the mixed, quenched product stream is converted by the digital computer into a signal effective in the micro-tuning of the temperature of regeneration gas for each reactor, whereby each reactor is brought promptly toward the targeted conversion for such reactor.

Each reactor in a bank of reactors 120, 220, etc. 620, 720, as shown in FIG. 1, contains an adiabatic bed of chromia-alumina particles and heat retentive alumina particles. The primary control 846, including the cycle timer, provides for the automatic cycling of the process steps amongst the seven reactors. After an adiabatic bed in a reactor has been heated to an appropriately hot temperature by the flow of hot regeneration gas, such bed may be vacuum purged to remove air and combustion gases and optionally treated with a reducing gas to reduce the chromium oxide catalytic component to a lower valent state more effective as a catalyst. In an adiabatic dehydrogenation method, each bed is prepared for the dehydrogenation portion of the cycle by an appropriate treatment.

The dehydrogenation portion of the cycle is initiated by the opening of the valve permitting hydrocarbon to flow from manifold supply line 101, generally maintained at subatmospheric pressure. In previous decades, the market prices of paraffins and unsaturated hydrocarbons has been such that the adiabatic method has been particularly attractive for the conversion of butane to butadiene, but the method has engineering advantages for the manufacture of unsaturated hydrocarbons for which the demand is sufficiently reliable to merit the type of capital investment involved in a plant for adiabatic dehydrogenation. In a typical butadiene plant, the complete cycle is 21 minutes, as regulated by the cycle timer of the primary control system 846. The regeneration time and dehydrogenation time are each about 560 seconds (9 1/5 minutes) and the balance of the 21 minute cycle time is required for the various intermediate and purging steps.

The effluent product stream from a reactor is withdrawn from a reactor and directed to a product manifold line 842. During a 21 minute cycle time, product effluent is collected from each of the seven reactors. Such mixed product stream is subjected to a quenching zone 843 to provide a stream of quenched, mixed product from the 7 reactors. Such mixed product stream has certain varying characteristics indicative of the extent of conversion in the reactors, and the measuring device for detecting such conversion is designated as a meter 844. After monitoring the conversion, the mixed, quenched product stream passes to the steps effective for the purification of the unsaturated hydrocarbon product 845.

AFter the dehydrogenation step in each reactor, there is appropriate purging of the hydrocarbon vapor, and the beginning of the regeneration, involving the injection of air effective in burning the coke deposited during the previous dehydrogenation portion of the cycle and having a sufficiently high temperature to provide heat transfer from the heated air to the catalyst bed. such hot air for regeneration flows through manifold line 108 from air heater 106. Air flows through line 107 into air heater 106. The combustion of gaseous fuel (ordinarily methane) from fuel source 102 through valve 103 heats such air. The thus heated air leaves the air heater 106 through line 108. A temperature regulating control is adjustable so that the heated air is as hot as required. The valve 103 may be responsive to such temperature regulating control.

In the drawings, there are notations of valves connecting a reactor with a $C_4$ hydrocarbon stream, regeneration air and supplemental methane fuel. The final temperature of the adiabatic bed in a reactor is controlled in part by the temperature of the hot air in line 108 (regulated by valve 103 controlling the amount of methane supplied to the air heater) and by the amount of supplemental modifying gas injected into the regeneration air from modifying gas manifold 105. Ordinarily, methane is the modifying gas, thus increasing regeneration gas temperature, but sometimes steam is a cooling gas. sometimes two similar systems are employed so that either of such modifying gases may be injected. Reactors and the manifold and valve system to the reactor assure complete mixing of gas streams prior to contacting the catalyst bed. Thus, any methane injected through line 105 is substantially burned to heat the regeneration air before it reaches the catalyst bed.

The description heretofore of the method of dehydrogenating a $C_4$ hydrocarbon stream to form a mixture comprising butylene and butadiene corresponds generally to the adiabatic dehydrogenation method as practiced in certain units prior to the development of the present invention.

Particular attention is directed to a digital computer 847 having an input signal through line 848 to the instrument for measuring the momentary extent of conversion at meter 844. The measurements of conversion as determined in the meter 844 are converted or transformed by the digital computer into a series of determinations of the deviation of each reactor from the average conversion and into a series of determinations of the deviation of such average conversion from the targeted conversion for that reactor and a series of signals, each signal being for a reactor a summation of such conversion deviation and such targeted deviation. During and/or immediately after the butadiene formation step, the digital computer determines from the data on the previous complete cycle, the average conversion and the deviation from average conversion for the reactor imminently scheduled for regeneration and determines from such data an appropriate correction factor, using also the data on the targeted conversion (set point) for such reactor, which correction factor may be zero, or a small positive or negative value applicable to the micro-tuning of the temperature of the regeneration gas for said reactor imminently scheduled for regeneration. The digital computer, by responding to the conversion measurements in the mixed, quenched product, provides the signals controlling the valve directinng the modifying gas (steam or methane) into the regeneration gas for the reactor undergoing regeneration, and thus controls the final temperature of the adiabatic bed, and thus regulates the extent of conversion in the next dehydrogenation cycle. The computer also sends a signal to adjust air heater temperature when appropriate.

Because the digital computer thus regulates the amount of modifying gas (methane or steam) sent to the regeneration gas for each of the reactors during regeneration, the reactors are brought toward the targeted conversion for each reactor, and thus ordinarily toward perfect balance amongst the reactors. As a result of the balancing by the computer, the range of deviation from targeted conversion amongst the seven reactors is significantly narrowed and is assuredly narrowed to within a range of plus or minus 5 per cent of the targeted conversion for each reactor. Heretofore, difficulties have been encountered in seeking to achieve the type of balance permitting optimum operation of the dehydrogenation plant, but the present invention assures better routine operation than was previously the general practice.

The mixed product stream, during each 9 1/5 minute period, has product from each of four reactors, thus complicating the problem of using the meter 844 to measure a characteristic indicative of conversion and identifying the measurement of conversion for each of the seven reactors. The approximate deviation in conversion for each reactor is derived from seven successive measurements during 1/7 of the cycle time when there are seven reactors or n measurements of one-nth of the cycle time when there are n reactors. The period of dehydrogenation corresponds approximately to 3/7's of the cycle time, or a plurality of the 1/nth fractions of the cycle time. Every three minutes, or 1/nth cycle time, a new deviation for a different time period is thus generated.

The relationship amongst the deviations from average conversion can be expressed by seven simultaneous equations as follows in which the maximum conversion during a three minute period is measured for 7 such periods and averaged and the deviations for each 3 minute period are designated as the $\Delta R$. From the $\Delta R$ data, the deviations for each reactor, designated as $\Delta r$, are determined from the simultaneous equations. The reactors are numbered in the order in which they go onstream.

$$\Delta R_1 = 1/3 \, (\Delta r_1 + \Delta r_2 + \Delta r_3)$$
$$\Delta R_2 = 1/3 \, (\Delta r_2 + \Delta r_3 + \Delta r_4)$$
$$\Delta R_3 = 1/3 \, (\Delta r_3 + \Delta r_4 + \Delta r_5)$$
$$\Delta R_4 = 1/3 \, (\Delta r_4 + \Delta r_5 + \Delta r_6)$$
$$\Delta R_5 = 1/3 \, (\Delta r_5 + \Delta r_6 + \Delta r_7)$$
$$\Delta R_6 = 1/3 \, (\Delta r_6 + \Delta r_7 + \Delta r_1)$$
$$\Delta R_7 = 1/3 \, (\Delta r_7 + \Delta r_1 + \Delta r_2)$$

The computer employs this set of simultaneous equations to determine the deviation for the seventh (imminently scheduled for regeneration) reactor, and generates a correction signal which is the summation of such deviation from average conversion and the deviation of the targeted conversion from average conversion. When regeneration temperature for a reactor such as $r_1$, has been corrected between period $R_1$ and period $R_5$, an appropriate approximate correction is applied for equations $R_6$ and $R_7$ to preserve the requirement for only seven unknowns from the seven equations.

The digital computer can solve such simultaneous equation for determining $\Delta r_7$ and/or each of the seven approximate reactor deviations from average conversion. Such deviation is desirably very small. Heretofore in the absence of the present invention, butadiene plants have been operated at conditions at which a reactor deviation of the magnitude of 10 per cent has sometimes occurred several times per year. By reducing maximum monthly reactor deviations to as low as 5 per cent, significant improvements are achieved, and still better results are obtained when the 14,400 reactor deviations per month are consistently less than about 1 per cent when all reactors are set for the same targeted conversion, and the deviations from average conversion are the only significant deviations.

By the use of the digital computer, the range of deviations from average conversion can be narrowed significantly so that the range of reactor deviations can be desirably about plus or minus 1 per cent and assuredly within the range of plus or minus 5 per cent. The automated control for minimizing unbalance amongst the conversion of the reactors permits more satisfactory operation of a bank of reactors. The computer control of regeneration gas temperature on an individual reactor individual regeneration basis also makes it feasible to adjust targeted conversion on an individual reactor individual dehydrogenation period basis. Shifts of a reactor or bank of reactors from one conversion level to another can be rate adjusted by controls of the type conveniently designated as ramp slope controls.

Ordinarily, the primary controls regulate the valve 103 so that the temperature of the air heater 106 is low enough that an amount of supplemental fuel is required during regeneration of each reactor. Moreover, the temperature of the hot air, containing some combustion gases, in line 108 is hot enough that the combination of such hot air and the thus ignited supplemental fuel from manifold line 105 is sufficient to raise the adiabatic bed to the temperature necessary for appropriate conversion in the next dehydrogenation step. The digital computer desirably includes a line 161 as a supplemental control signal for valve 103 so that the temperature of the hot air in line 108 is within the range necessary for the microtuning signals 151, 251, etc. 751, to maintain the desired balance amongst the reactors. The signal from the computer to the air heater can modify the temperature regulating control which in turn adjusts the methane supply to the air heater. Under those circumstances in which the air heater, in order to meet the needs of another reactor, supplies air which is too hot, the regeneration gas for a particular reactor can be cooled by injection of a cooling gas at a temperature significantly cooler (at least about 500°F. cooler) than the hot air from the air heater. Compressed air is suitable as a cooling gas. Oftentimes it is convenient to use steam at about 300°F. as such cooling gas.

The nature of the invention is further clarified by a plurality of examples.

EXAMPLE 1

Fresh catalyst is supplied at a turn-around to each of seven reactors 120–720. A hydrocarbon feed, consisting of a mixture of fresh butane and recycled $C_4$ hydrocarbons (comprising butene-1, butene-2, and butane from purification system 845), is supplied through line 101. Each bed is brought to thee desired operating temperature (1075°F.) and evacuated. The cycle timer controls the valves so that the hydrocarbon flows through each reactor for about 9 1/5 minutes, during which the dehydrogenation effluent flows from the reactor through a valve and through a reactor pipe and through a collection line of a manifold 842 to the quenching zone 843, wherein the gas temperature is cooled from the 1075°F. level to about 100°F. The mixed, quenched gas stream is directed through meter 844. After such metering, the gas stream is sent to the purification system 845 in which butadiene and/or other products are recovered and purified.

Each reactor is purged and prepared for regeneration. During regeneration, hot air flows to a reactor through line 108, whereby the coke deposited in the reactor is burnt. Before and/or during the regeneration of reactor 120, the digital computer 847 provides a signal for the correction of the temperature of the regeneration gas supplied to reactor 120. Ordinarily, no change in the adjustment of valve 103 for air heater will be needed. Usually it will not be necessary to cool the gas by dilution with a cooling gas such as steam at about 300°F. Oftentimes the computer signal controls the micro-tuning of valve 123. The amount of methane supplied from line 105 is thus adjusted so that the conversion during the next dehydrogenation step will more closely match the targeted conversion for said reactor 120.

In accordance with some embodiments of the present invention, the density of the mixed, quenched gas stream is measured by meter 844 to detect an indication of conversion for the three minute period. It is sometimes advantageous to use the maximum conversion during such period as the desired indication. The memory of the computer notes such indication of conversion for each of the seven periods of 3 minutes each and obtains the average conversion for such seven measurements of the 21 cycle period, as well as the seven deviations for the seven periods, the $\Delta R$'s of seven simultaneous equations. The computer determines, for the reactor imminently scheduled for regeneration, the deviation from average conversion as well as the deviation of such average conversion from targeted conversion. Moreover, the computer determines the summation of said two deviations. Usually each reactor in a bank of reactors is set for the same targeted conversion, but the individual control of regeneration by the computer of the present invention makes more appropriate the individual adjustment of targeted conversion for each reactor.

The computer generates for the reactor imminently scheduled for regeneration a correction signal which is related to a signal constituting said summation of the deviation of the reactor from average conversion and the deviation of targeted conversion from average conversion. If the correction signal is negative, indicating that there was more conversion in a particular reactor than targeted, then during the next regeneration period there should be a decrease in the temperature of the regeneration gas by decreasing the amount of methane supplied to such reactor. Line 151 represents the signal from the computer 847 to valve 123 for achieving such micro-tuning control. If a sufficient lowering of regeneration temperature were not feasible, then the computer would send a supplemental correction signal by line 161 to valve 103 of air heater 106. if a sufficient lowering of the temperature of the regeneration gas were not feasible by the signals through 151 and 161, then the computer would actuate the system for injecting a cooling gas into the regeneration gas stream directed to such reactor. An example of a modifying gas having a cooling action would be steam at about 300°F.

EXAMPLE 2

In a seven reactor system not initially equipped for the practice of the present invention, the gas density of the quenched, mixed product is measured during each 3 minutes during an appropriate time period. Such data are employed with the set of simultaneous equations previously described to determine reactor deviations for each of the seven reactors. The reactor deviations are tabulated to evaluate the range of reactor deviations. It is found that the range of gas gravity deviation is from −0.18 to about 0.018. The thus measured values are as follows:

| Reactor No. | Gravity Deviation |
|---|---|
| 1 | −0.018 |
| 2 | −0.002 |
| 3 | +0.002 |
| 4 | +0.012 |
| 5 | −0.002 |
| 6 | +0.018 |
| 7 | −0.01 |

Such data illustrate the method of calculating average gas density during each three minute period and the method for calculating reactor deviation by the method of the present invention. Such data also illustrate the phenomena of a range of unbalance of the magnitude of plus or minus 0.02 gas gravity units in the absence of the present invention. The range of reactor deviation is narrowed by adoption of the present invention to about plus or minus 0.005 gas gravity units. Such superior balancing amongst reactors improves daily performance of the system and permits setting the targeted conversion for the bank of reactors at a higher conversion level than would have been risked without the present invention.

EXAMPLE 3

A butadiene plant is designed to employ six reactors on a 24 minute cycle. The mixed, quenched dehydrogenation effluent is measured for density using a meter responsive to the instantaneous gas density of the flowing stream and the signals from the density meter are transmitted to the computer in which reactor deviations from targeted conversion for each reactor are automatically determined from such density measurement signals. The summation of the approximate deviation from average conversion and the deviation of the targeted conversion from such average conversion provides the deviation signal for each reactor, which signal is employed by the computer to control the micro-tuning of the valves for the injection of a modifying gas (methane or a cooling gas such as steam) during the next regeneration of such reactor.

EXAMPLE 4

A butadiene plant is designed to employ eight reactors on a 24 minute cycle. A meter measuring the hydrogen content of the mixed, quenched dehydrogenation effluent is employed to detect instantaneous variations in conversion and the signals from such meter are translated by the computer into correction signals controlling the micro-tuning of the supplemental methane valve during regeneration. In this manner, the balance amongst the reactors is enhanced so that the range of deviation in conversion amongst the eight reactors is transformed from about 7 per cent to about 0.5 per cent.

EXAMPLE 5

The dehydrogenation effluent from each of seven reactors is connected to a manifold system comprising a plurality of collection lines from the reactors and a common manifold line. A meter responsive to the instantaneous concentration of hydrogen in the gas stream is installed in a collection line from a reactor to a manifold line. At this zone, the gas temperature is so high as to be unsuitable for some types of instrumentation, but within the operating range of the hydrogen meter. Each valve for the modifying gas (e.g., supplemental methane) and the air heater temperature is micro-tuned in response to the signal generated in the computer in response to the indication of overall conversion in said particular reactor, as measured by the hydrogen meter during the immediately preceding dehydrogenation period. The computer determines a signal which is a summation of the deviation of the average conversion from targeted conversion and the deviation of conversion of such reactor from average conversion. Such direct measurement of conversion in a particular reactor, and use of the computer to control the regeneration in an effort to restore more nearly to its targeted conversion involves measurements in zones in which instrumentation difficulties might occur. Instrumentation and communication lines are provided for an alternative mode of operation. The mixed, quenched dehydrogenation effluent is directed through a zone in which the conversion during 1/nth of cycle period is measured by a densometer and the signals are transmitted to the computer. The deviations of each 1/nth of cycle time are employed by the computer to determine for the reactor imminently scheduled for regeneration a signal indicative of approximate deviation for each reactor from average conversion and a signal indicative of the deviation of average conversion from targeted conversion, and a signal which is the summation of such deviations. These signals are employed for regulating the valves for methane at the air heater and the supplemental methane for the individual reactor, thereby adjusting the reactor more closely to its targeted conversion. The effectiveness of the mode of operation featuring the measurement of gas density in the quenched, mixed stream is confirmed so that such indirectly determined summation of the two approximate deviations for a particular reactor is a practical alternative to a direct measurement of conversion in the dehydrogenation effluent from a particular reactor. Lower maintenance costs for instrumentation and lower capital investment for instrumentation are among the important advantages achieved by using the measurement of the quenched, mixed stream.

In a control test, an attempt is made to measure ethe density of a sample stream withdrawn from the hot effluent from a particular reactor and directed through a miniature quench zone prior to passage through the measuring zone and return down-stream in the hot effluent. The miniature quench system provided for the stream of sampling gas complies with the engineering standards satisfactory for instrumentation for several high temperature processes. However, the ease of polymerization and carbonization of components of the butadiene effluent stream made the attempted miniature quenching system quite unmanageable. The propensity for fouling up the miniature quenching system created excessive maintenance problems. The constrictions inherent in the sampling system significantly enhanced the probabilities of fouling of the miniature quenching system. By a series of tests it is established that the instrumentation for a butadiene plant should be positioned in a zone subsequent to the large quenched system or in the hot gas stream prior to quenching and that attempts to rely upon miniature quenching systems involve an objectionably high degree of unreliability, excessive cost, and other engineering disadvantages.

EXAMPLE 6

In a seven reactor system, the signals from the meter measuring conversion in the mixed, quenched dehydrogenation effluent are sent to a computer in which the signal processing involves storage in the memory of conversion data for a significant series of periods corresponding to 1/n cycle. The fluctuations in conversion are ordinarily within a relatively narrow range, so that signals relating to increments greater than the typical minimum provide useful data. At the end of each 1/nth cycle, the computer uses such data to determine average conversion and to determine appropriate deviations of conversion for each reactor (positive, negative, or zero) between such average conversion and reactor conversion. Deviation of targeted conversion from average conversion is also determined. The computer generates for the reactor imminently scheduled for regeneration indicative of the sum of the reactor deviation from average conversion and the deviation of average conversion from targeted conversion. A correction signal related to such summation signal actuates the micro-adjustment of the valves supplying modifying gas (e.g., cooling gas or fuel gas) for the regeneration for such reactor so that the post-regeneration temperature of the reactor is precisely controlled for each regeneration step. When necessary, the air heater temperature can be adjusted by such correction signal, and micro-tuning of the regeneration gas temperature can be adjusted by regulating the valve supplying modifying gas (supplemental methane or cooling gas) for the regeneration gas for such reactor. If all reactors are adjusted for the same targeted conversion, as has heretofore been ordinary, imperfections in balance amongst reactors are thus detected promptly, and because of such promptness of measurement of approximate deviation of each reactor, corrective adjustments can be made for the regeneration period following the dehydrogenation period during which the conversion measurements were made.

Various modifications in the invention are possible without departing from the scope of the appended claims.

We claim:

1. In a method of preparing unsaturated hydrocarbons from a gaseous hydrocarbon feedstock, wherein during a complete cycle the feedstock is directed through a dehydrogenation system comprising $n$ adiabatic reactor beds in parallel, $n$ being the number of adiabatic reactor beds in said system, said $n$ having the same numerical value throughout said system, and wherein the dehydrogenation effluent from each of the $n$ adiabatic reactor beds is mixed and directed through a quenching zone to provide a mixed, quenched product stream, which during the complete cycle time for one adiabatic reactor bed contains the mixture of product from all of said adiabatic reactor beds, said cycle time being arbitrarily divided into n instances of 1/nth of the cycle time, said system comprising primary controls for conducting said dehydrogenation to seek from each of said adiabatic reactor beds a targeted conversion of hydrocarbon feedstock, the improvement which consists of:

making a series of n measurements of a characteristic indicative of the conversion of hydrocarbon feedstock during 1/nth of cycle time;

determining the average characteristic indicative of the conversion from the n instances of thus measured characteristic of conversion, said time average characteristic indicative of the conversion being a measurement of the average conversion of all reactors during said cycle time;

determining the approximate positive or negative deviation of measurement of a characteristic indicative of conversion from said average characteristic indicative of conversion, said deviation being determined for each of the $n$ time periods;

utilizing said n deviations of time periods to determine for the adiabatic reactor bed imminently scheduled for regeneration the approximate positive or negative deviation of said adiabatic reactor bed from said average characteristic indicative of conversion;

determining for the adiabatic reactor bed imminently scheduled for regeneration the deviation of said targeted conversion from said average characteristic indicative of conversion;

generating for each adiabatic reactor bed as it is imminently scheduled for regeneration a summation signal indicative of the summation of conversion deviation of targeted conversion from average characteristic indicative of conversion and said approximate positive or negative deviation of said adiabatic reactor bed from said average characteristic indicative of conversion and generating a positive or negative correction signal related to said summation signal;

utilizing said correction signal for adjusting the temperature of the regeneration gas to said reactor during said scheduled regeneration at conditions adapted to restore as closely as feasible the conversion in said reactor in the subsequent cycle to said targeted conversions; and repeating such adjustment of the temperature of the regeneration gas to each reactor for each regeneration to maximize approach toward targeted conversion.

2. The method of claim 1 in which each of the $n$ reactors has substantially the same targeted conversion whereby the individual adjustment of regeneration gas temperature minimizes the imbalance of conversion amongst the n reactors over a prolonged period of time and preserves a conversion range which is smaller than about plus or minus 5 per cent for the $n$ reactor deviations in conversion during a complete cycle time.

3. The method of claim 1 in which said correction signal for a reactor regulates the amount of a modifying gas injected into the hot air directed to such reactor, said modifying gas being selected from the group consisting of fuel gas and a cooling gas having a temperature at least 500°F. cooler than the hot air flowing toward the reactor.

4. The method of claim 1 in which said correction signal for a reactor regulates at least one of at least two controls employed in regulating the temperature of the regeneration gas, one of said controls being for the fuel gas supplied to the air heater and another of said controls being for a modifying gas supplied to each reactor, said modifying gas being selected from the group consisting of fuel gas and a cooling gas having a temperature at least 500°F. cooler than the hot air flowing toward the reactor.

5. The method of claim 1 in which the density of the mixed, quenched product stream is the characteristic of such stream which is measured.

* * * * *